United States Patent
Nose et al.

(10) Patent No.: US 8,624,067 B2
(45) Date of Patent: Jan. 7, 2014

(54) PROCESS FOR PREPARING 2-CHLORO-3,3,3-TRIFLUOROPROPENE

(75) Inventors: Masatoshi Nose, Settsu (JP); Atsushi Suzuki, Settsu (JP); Tsuneo Yamashita, Settsu (JP); Kenichi Katsukawa, Settsu (JP)

(73) Assignee: Daikin Industries, Ltd., Osaka (JP)

( * ) Notice: Subject to any disclaimer, the term of this patent is extended or adjusted under 35 U.S.C. 154(b) by 142 days.

(21) Appl. No.: 13/259,828

(22) PCT Filed: Apr. 21, 2010

(86) PCT No.: PCT/JP2010/057530
§ 371 (c)(1),
(2), (4) Date: Sep. 23, 2011

(87) PCT Pub. No.: WO2010/123148
PCT Pub. Date: Oct. 28, 2010

(65) Prior Publication Data
US 2012/0022303 A1    Jan. 26, 2012

Related U.S. Application Data

(60) Provisional application No. 61/202,966, filed on Apr. 23, 2009.

(51) Int. Cl.
*C07C 17/25* (2006.01)
(52) U.S. Cl.
USPC ......................................... 570/155; 570/160
(58) Field of Classification Search
None
See application file for complete search history.

(56) References Cited

U.S. PATENT DOCUMENTS

| 7,795,480 B2 * | 9/2010 | Merkel et al. ................ 570/155 |
| 2009/0030247 A1 | 1/2009 | Johnson et al. |

FOREIGN PATENT DOCUMENTS

| WO | 2007/079431 | 7/2007 |
| WO | 2008/054781 | 5/2008 |
| WO | 2009/003084 | 12/2008 |
| WO | 2009/015317 | 1/2009 |

OTHER PUBLICATIONS

International Search Report issued Aug. 16, 2010 in International (PCT) Application No. PCT/JP2010/057530 of which the present application is the national stage.
Written Opinion of the International Searching Authority issued Aug. 16, 2010 in International (PCT) Application No. PCT/JP2010/057530 of which the present application is the national stage.

* cited by examiner

*Primary Examiner* — Sudhakar Katakam
(74) *Attorney, Agent, or Firm* — Wenderoth, Lind & Ponack, L.L.P.

(57) ABSTRACT

The present invention provides a process for preparing 2-chloro-3,3,3-trifluoropropene including subjecting, in the absence of a catalyst, at least one chlorine-containing compound selected from the group consisting of chloropropane represented by formula (1): $CClX_2CHClCH_2Cl$, wherein each X is the same or different and each represents Cl or F, chloropropene represented by formula (2): $CClY_2CCl=CH_2$, wherein each Y is the same or different and each represents Cl or F, and chloropropene represented by formula (3): $CZ_2=CClCH_2Cl$, wherein each Z is the same or different and each represents Cl or F, to a reaction with hydrogen fluoride under heating in a gas phase. According to the present invention, 2-chloro-3,3,3-trifluoropropene (HCFC-1233xf) can be effectively prepared by an easy and economically advantageous process that is suitable for industrial scale production.

8 Claims, 2 Drawing Sheets

PROCESS FOR PREPARING 2-CHLORO-3,3,3-TRIFLUOROPROPENE

This application is a national stage application of International Application No. PCT/JP2010/057530, filed Apr. 21, 2010, which claims priority to U.S. provisional Application No. 61/202,966, filed Apr. 23, 2009.

TECHNICAL FIELD

The present invention relates to a process for preparing 2-chloro-3,3,3-trifluoropropene.

BACKGROUND ART

2-Chloro-3,3,3-trifluoropropene (HCFC-1233xf) represented by the formula $CF_3CCl=CH_2$ is a compound that is useful as an intermediate for producing various kinds of fluorocarbons, and also as a monomer component of various kinds of polymers.

A known process for preparing HCFC-1233xf comprises reacting anhydrous hydrogen fluoride (HF) in a gas phase in the presence of a catalyst. For example, Patent Literature (PTL) 1 listed below discloses a process comprising fluorination of 1,1,2,3-tetrachloropropene (HCC-1230xa, $CCl_2=CClCH_2Cl$) in a gas phase in the presence of a chromium-based catalyst. Patent Literature 2 listed below also reports a process comprising fluorination of 1,1,2,3-tetrachloropropene in a gas phase using a chromium-based catalyst. Further, Patent Literature 3 teaches that 1,1,2,3-tetrachloropropene (HCC-1230xa), 1,1,1,2,3-pentachloropropane (HCC-240db), 2,3,3,3-tetrachloropropene (HCC-1230xf), etc. can be fluorinated in the presence of a stabilizer for minimizing catalyst deterioration.

However, the processes disclosed in the above literature suffer from various disadvantages. For example, further improvement in the yield of HCFC-1233xf is required, the use of a catalyst is costly, and many products are produced by the reaction in addition to the target product of HCFC-1233xf, resulting in unsatisfactory selectivity. Further, since catalytic activity tends to decrease as a reaction proceeds, there have been many attempts to use a stabilizer for the purpose of minimizing catalyst deactivation.

Patent Literature 4 discloses a process comprising reacting 1,1,2,3-tetrachloropropene (HCC-1230xa) with anhydrous hydrogen fluoride (HF) in a liquid phase in the presence of a halogenated antimony catalyst. However, this process is unsuitable for industrial production, because handling the catalyst is difficult, the process is uneconomical due to the occurrence of reactor corrosion, necessity for waste treatment, etc., and dealing with the process is problematic. Patent Literature 5 reports that HCFC-1233xf can be prepared by reacting 1,1,2,3-tetrachloropropene (HCC-1230xa) with anhydrous hydrogen fluoride (HF) in a liquid phase in the absence of a catalyst. However, this process is not suitable for industrial-scale production, because a longer reaction time is required as a result of its low reaction rate, an overly large amount of HF is necessary, severe reaction conditions under high pressure are necessitated, etc.

As described above, a process by which HCFC-1233xf is easily and economically prepared at a high yield has not yet been established.

CITATION LIST

Patent Literature

PTL 1: WO 2007/079431 A2
PTL 2: WO 2008/054781 A1
PTL 3: WO 2009/015317 A1
PTL 4: US 2009/0030247 A1
PTL 5: WO 2009/003084 A1

SUMMARY OF INVENTION

Technical Problem

The present invention has been accomplished in view of the current status of the foregoing prior art. The main object of the present invention is to provide a process capable of effectively preparing 2-chloro-3,3,3-trifluoropropene (HCFC-1233xf), the process being easily conducted, economically advantageous, and suitable for industrial scale production.

Solution to Problem

The present inventors conducted extensive research to achieve the above object. As a result, the present inventors found the following. That is, a process in which a chloropropane or chloropropene compound represented by a specific formula is used as a starting material and is subjected to a reaction with hydrogen fluoride under heating in a gas phase in the absence of a catalyst can prepare the target HCFC-1233xf at a high yield in a single reaction step within a relatively short reaction time while eliminating the drawbacks of known preparation processes of HCFC-1233xf. Thus, the process enables efficient production on an industrial scale. The present invention has been accomplished in view of the above findings.

Specifically, the present invention provides a process for preparing 2-chloro-3,3,3-trifluoropropene, as summarized below.

1. A process for preparing 2-chloro-3,3,3-trifluoropropene comprising subjecting, in the absence of a catalyst, at least one chlorine-containing compound selected from the group consisting of chloropropane represented by formula (1): $CClX_2CHClCH_2Cl$, wherein each X is the same or different and each represents Cl or F, chloropropene represented by formula (2): $CClY_2CCl=CH_2$, wherein each Y is the same or different and each represents Cl or F, and chloropropene represented by formula (3): $CZ_2=CClCH_2Cl$, wherein each Z is the same or different and each represents Cl or F, to a reaction with hydrogen fluoride under heating in a gas phase.

2. The process for preparing 2-chloro-3,3,3-trifluoropropene according to Item 1, wherein the chlorine-containing compound used as a starting material is at least one compound selected from the group consisting of 1,1,1,2,3-pentachloropropane, 2,3,3,3-tetrachloropropene, and 1,1,2,3-tetrachloropropene.

3. The process for preparing 2-chloro-3,3,3-trifluoropropene according to Item 1 or 2, wherein the hydrogen fluoride is used in an amount of 5 to 30 mol relative to 1 mol of the chlorine-containing compound used as a starting material, and the reaction is carried out at 300° C. to 500° C.

4. A process for preparing 2-chloro-3,3,3-trifluoropropene, comprising the step of, after the preparation of 2-chloro-3,3,3-trifluoropropene in accordance with the process of any of Items 1 to 3, recycling at least one chlorine-containing compound contained in a product obtained during the preparation and selected from the group consisting of the chloropropane represented by formula (1): $CClX_2CHClCH_2Cl$, wherein each X is the same or different and each represents Cl or F, the chloropropene represented by formula (2): $CClY_2CCl=CH_2$, wherein each Y is the same or different and each represents Cl or F, and the chloropropene represented by formula (3): $CZ_2=CClCH_2Cl$, wherein each Z is the same or different and each represents Cl or F, as a starting compound.

Hereinafter, the process for preparing 2-chloro-3,3,3-trifluoropropene of the present invention is described in more detail.

(1) Starting Compound

In the present invention, at least one chlorine-containing compound selected from the group consisting of chloropropane represented by formula (1): $CClX_2CHClCH_2Cl$, wherein each X is the same or different and each represents Cl or F, chloropropene represented by formula (2): $CClY_2CCl=CH_2$, wherein each Y is the same or different and each represents Cl or F, and chloropropene represented by formula (3): $CZ_2=CClCH_2Cl$, wherein each Z is the same or different and each represents Cl or F, is utilized as a starting compound. By subjecting the chlorine-containing compound used as a starting material to a reaction with hydrogen fluoride under the conditions mentioned below, a target 2-chloro-3,3,3-trifluoropropene (HCFC-1233xf) can be prepared in a single reaction step at a high yield.

Of the aforementioned starting compounds, specific examples of chloropropane represented by formula (1): $CClX_2CHClCH_2Cl$ include $CCl_3CHClCH_2Cl$ (HCC-240db, bp. 179° C./760 mmHg, 51° C. to 53° C./3 mmHg), $CFCl_2CHClCH_2Cl$ (HCFC-241db, bp. 157° C.), $CF_2ClCHClCH_2Cl$ (HCFC-242dc, bp. 113° C. to 114° C.), and the like; specific examples of chloropropene represented by formula (2): $CClY_2CCl=CH_2$ include $CCl_3CCl=CH_2$ (HCC-1230xf, bp. 128° C.), $CFCl_2CCl=CH_2$ (HCFC-1231xf, bp. 98.5° C. to 99° C.), $CF_2ClCCl=CH_2$ (HCFC-1232xf, bp. 57° C. to 58° C.), and the like; and specific examples of chloropropene represented by formula (3): $CZ_2=CClCH_2Cl$ include $CCl_2=CClCH_2Cl$ (HCC-1230xa, bp. 138° C.), $CFCl=CClCH_2Cl$ (HCFC-1231xb), $CF_2=CClCH_2Cl$ (HCFC-1232xc), and the like.

Of the above starting compounds, HCC-240db ($CCl_3CHClCH_2Cl$ (1,1,1,2,3-pentachloropropane)), HCC-1230xf ($CCl_3CCl=CH_2$ (2,3,3,3-tetrachloropropene)) and HCC-1230xa ($CCl_2=CClCH_2Cl$ (1,1,2,3-tetrachloropropene)) are particularly advantageous, because these compounds are easily obtainable and inexpensive.

In the present invention, the aforementioned starting compounds can be used singly or in a combination of two or more.

(2) Reaction Method

The preparation process of the present invention comprises subjecting the aforementioned starting compound to a reaction with hydrogen fluoride under heating in a gas phase in the absence of a catalyst.

The reaction of the aforementioned starting compound with hydrogen fluoride under the conditions mentioned above can prepare a target 2-chloro-3,3,3-trifluoropropene (HCFC-1233xf) in a single reaction step with high selectivity.

In the preparation process of the present invention, it is important that the aforementioned starting compound undergoes a reaction with hydrogen fluoride in a gas phase. The starting compound may be, however, in a liquid phase at the time of supply, insofar as the starting compound is in a gas phase when brought into contact with hydrogen fluoride in the reaction temperature region mentioned below. For example, when the starting compound is liquid at normal temperature under normal pressure, the starting compound is evaporated with an evaporator (evaporation region) and is subsequently allowed to pass through a preheating region to be supplied to a mixing region where it is brought into contact with anhydrous hydrogen fluoride. This enables the reaction to be carried out in a gas phase. The reaction may also be carried out by supplying the starting compound in a liquid phase to a reactor, and evaporating the compound when the compound enters a reaction region to react with hydrogen fluoride. There is no limitation to the method for evaporating the starting compound in the reaction region. The starting compound may be evaporated into a gas phase by, for example, filling a reaction tube with a material that exhibits excellent thermal conductivity, exerts no catalytic activity in the reaction of the present invention, and is stable to hydrogen fluoride, such as nickel beads, Hastelloy pellets, or the like, so as to homogenize the temperature distribution within the reaction tube, heating the reaction tube to not less than the evaporation temperature of the starting compound, and supplying the starting compound in a liquid phase thereinto.

Hydrogen fluoride is usually fed to the reactor in a gas phase with the starting compound. The amount of hydrogen fluoride is generally about 3 mol or more, preferably from about 5 to about 100 mol, and more preferably from about 5 to about 30 mol, per 1 mol of the starting compound. This amount range can maintain both the conversion rate of the starting compound and the selectivity of HCFC-1233xf within a desirable range.

The aforementioned starting material may be fed to the reactor as is, or may be diluted with an inert gas, such as nitrogen, helium, argon or the like, to be fed to the reactor.

There is no limitation to the form of the reactor used in the process of the present invention. Examples of usable reactors include a hollow adiabatic reactor, an adiabatic reactor packed with a porous or nonporous metal or medium that improves the gas-phase mixing state between hydrogen fluoride and the starting material. Also usable is a multitubular reactor in which a heat transmitting medium is used to cool the reactor and to homogenize the temperature distribution within the reactor. In the case where a hollow reactor is utilized, when a reaction tube having a smaller inner diameter is used to improve heat transfer efficiency, it is preferable, for example, that the ratio of the flow rate of the starting material to the inner diameter of the reaction tube is adjusted so that the linear velocity is high and the heat transfer area is large.

It is preferable that the reactor be formed of a material that is resistant to the corrosive action of hydrogen fluoride, such as HASTELLOY®, INCONEL®, MONEL®, and INCOLOY®.

In the process of the present invention, the temperature in the reactor is generally about 250° C. to about 600° C., preferably about 300° C. to about 500° C., and more preferably about 350° C. to about 450° C. When the temperature exceeds the upper limit of this temperature range, the selectivity of HCFC-1233xf will be undesirably reduced, and reactor corrosion will tend to be accelerated. When the temperature is lower than the lower limit of this temperature range, the conversion rate of the starting compound will undesirably decrease. When the reaction is performed at a temperature higher than 450° C., carbide may be generated and adhere to or be deposited on the reaction tube wall or filler, which gradually clogs the inside of a reactor. In this case, the carbide residue in the reaction tube may be removed by combustion by introducing oxygen into the reaction system together with the starting compound, or by halting the reaction once and allowing oxygen or air to pass through the reactor.

There is no limitation to the pressure during the reaction insofar as the aforementioned starting compound and hydrogen fluoride are present in a gas phase. The reaction may be carried out under any pressure, i.e., normal pressure, increased pressure, or reduced pressure. Specifically, the preparation process of the present invention may be conducted under reduced pressure or atmospheric pressure (0.1

MPa), and may also be conducted under increased pressure so long as the starting material does not turn into the liquid phase.

There is no particular limitation to the reaction time, but the contact (residence) time, which is generally determined by $V/F_0$, may be adjusted to a range of 0.1 to 100 sec, preferably about 1 to about 30 sec. $V/F_0$ is a ratio of a reaction volume V (cc), i.e., a volume of a reaction space, in a gas phase to a total flow rate $F_0$ (flow rate at 0° C., 0.1 MPa: cc/sec) of starting material gases (starting compound, hydrogen fluoride and an inert gas) introduced into the reaction system.

Under the above reaction conditions, a reaction product comprising $CF_3CCl=CH_2$ (2-chloro-3,3,3-trifluoropropene, HCFC-1233xf) can be obtained at the reactor outlet. HCFC-1233xf may be collected after being purified by distillation or another method. The collected product may be used for a desired purpose as is, or may be converted into another compound.

In the production process of the present invention, the reaction product contains, in addition to HCFC-1233xf, $CCl_2=CClCH_2Cl$ (HCC-1230xa), $CCl_3CCl=CH_2$ (HCC-1230xf), $CFCl_2CHClCH_2Cl$ (HCFC-241db), $CFCl_2CCl=CH_2$ (HCFC-1231xf), $CF_2ClCHClCH_2Cl$ (HCFC-242dc), $CF_2ClCCl=CH_2$ (HCFC-1232xf), and the like. These compounds are produced as precursors of HCFC-1233xf, depending on the type of starting material used and the reaction conditions employed, and are all usable as a starting material in the preparation process of the present invention.

In the production process of the present invention, after HCFC-1233xf is isolated and collected, the above precursors contained in the reaction product and the unreacted starting materials, i.e., the chlorine-containing compounds represented by formulae (1), (2) and (3), may be returned to the reactor, so that they can be recycled and reused as starting materials. As described above, by recycling the precursors of HCFC-1233xf and the unreacted starting materials, even if the conversion rate of the starting materials is low, a high productivity can be maintained.

Advantageous Effects of Invention

According to the process of the present invention, 2-chloro-3,3,3-trifluoropropene (HCFC-1233xf) can be prepared in a single step reaction at a remarkably high yield with relatively short contact time by using a chlorine-containing compound represented by a specific formula as a starting material.

Further, the process of the present invention can be performed under mild conditions, i.e., normal pressure, reduced pressure, or the like, and it utilizes a gas phase reaction that is suitable for continuous preparation.

In addition, the process of the present invention eliminates the defects that occur in the known preparation processes utilizing catalysts. The target 2-chloro-3,3,3-trifluoropropene can be obtained with higher selectivity.

As described above, the process of the present invention is highly advantageous for industrial application for preparing 2-chloro-3,3,3-trifluoropropene (HCFC-1233xf).

DESCRIPTION OF EMBODIMENTS

Hereunder, the present invention is described in more detail with reference to Production Examples of 1,1,1,2,3-pentachloropropane (HCC-240db), 1,1,2,3-tetrachloropropene (HCC-1230xa), and 2,3,3,3-tetrachloropropene (HCC-1230xf), which are used as starting materials, and with reference to Examples of the present invention.

Production Example 1

1,1,1,2,3-Pentachloropropane (HCC-240db) was prepared by sequentially performing the following Steps (1) to (3).

(1) Preparation Step of 1,1,1,3-tetrachloropropane (HCC-250fb)

A 1,000 ml autoclave equipped with a thermometer, a vacuum line, a nitrogen purge line, a feeding line, a gauge, and a pressure relief valve was charged with 9.72 g (171 mmol) of soft iron powder, 48 g (260 mmol) of triethyl phosphate, 200 mg of ferric chloride, and 810 g (5.26 mol) of carbon tetrachloride, and was purged 5 times with nitrogen, and once with ethylene. The autoclave was then evacuated and charged, under stirring, with ethylene to a gauge pressure of 0.4 MPa. When the autoclave was heated to 110° C., the reaction was initiated, and the internal temperature was increased to 134° C., while the pressure was decreased from 0.8 MPa to 0.25 MPa. The ethylene pressure was maintained at 0.8 MPa, and stirring was performed at an internal temperature of 120° C. for 9 hours. Thereafter, 24 g (130 mmol) of triethyl phosphate was injected into the autoclave, and the reaction was allowed to proceed at 120° C. for 7 hours.

After completion of the reaction, the crude product was analyzed by gas chromatography, and complete consumption of carbon tetrachloride was thereby confirmed. The crude product was washed twice with water having a volume 3 times that of the crude product, and the organic layer was dried over magnesium sulfate to obtain HCC-250fb having a purity of 79.8%, as determined by gas chromatography. The by-product was an oligomer in which HCl was added to ethylene.

The obtained crude product was distilled under reduced pressure (10 mmHg), and a fraction at 70° C. to 74° C. was collected to obtain 814 g of HCC-250fb at a purity of 98% or more (4.94 mol, yield: 91%).

(2) Preparation Step of 1,1,3-trichloropropene (HCC-1240za) and 3,3,3-trichloropropene (HCC-1240zf)

A 1,000 ml four-necked flask equipped with a thermometer and a condenser tube was charged with 540 g (3.0 mol) of HCC-250fb obtained in Step (1) above, 630 g of 40% aqueous KOH solution, and 10 g of phase-transfer catalyst (Aliquat 336). The reaction was allowed to proceed under stirring at 80° C. in an oil bath for 3 hours. After completion of the reaction, the resulting product was cooled and distilled under reduced pressure (10 to 20 mmHg), and a fraction at 67.7° C. to 81.9° C. was collected to obtain 390 g of a mixture of HCC-1240zf and HCC-1240za (HCC-1240zf:HCC-1240za=62:38 (2.68 mol, yield: 89.3%)).

(3) Preparation Step of 1,1,1,2,3-pentachloropropane (HCC-240db)

A 500 ml flask equipped with a high-pressure mercury vapor lamp, a magnetic stirrer and two gas ports was charged with 265 g of the mixture of the 1,1,3-trichloropropene (HCC-1240za) and 3,3,3-trichloropropene (HCC-1240zf) obtained in Step (2) above, which was allowed to cool to 0° C. in an ice bath. The content was stirred under irradiation with ultraviolet light, and chlorine gas was introduced at 20 to 120 mL/min from one of the gas ports to the area above the liquid surface of the content. The reaction mixture was intermittently sampled, and analyzed by gas chromatography to measure the degree of chlorination. Three hours later, the trichloropropene was entirely consumed, and 370 g of product was obtained. The obtained product was distilled under reduced pressure (3 mmHg), and a fraction at 51° C. to 53° C. was collected to obtain 330 g of 1,1,1,2,3-pentachloropropane (HCC-240db) at a purity of 99.6%.

Production Example 2

The following process was performed to prepare a mixture of 1,1,2,3-tetrachloropropene (HCC-1230xa) and 2,3,3,3-tetrachloropropene (HCC-1230xf).

Preparation Process of 1,1,2,3-tetrachloropropene (HCC-1230xa) and 2,3,3,3-tetrachloropropene (HCC-1230xf)

A 1,000 ml four-necked flask equipped with a thermometer and a condenser tube was charged with 330 g (1.52 mol) of 1,1,1,2,3-pentachloropropane (HCC-240db) obtained in Step (3) of Production Example 1, 310 g of 40% aqueous KOH solution, and 6 g of phase-transfer catalyst (Aliquat 336). The reaction was allowed to proceed under stirring at 80° C. in an oil bath for 3 hours. After completion of the reaction, the resulting product was cooled and distilled under reduced pressure (1 mmHg), and a fraction at 20° C. to 22° C. was collected to obtain 259 g of a mixture of HCC-1230xa and HCC-1230xf (HCC-1230xa:HCC-1230xf=38:62 (1.44 mol, yield: 94.8%)) at a purity of 99.9%.

Example 1

Figure 1:
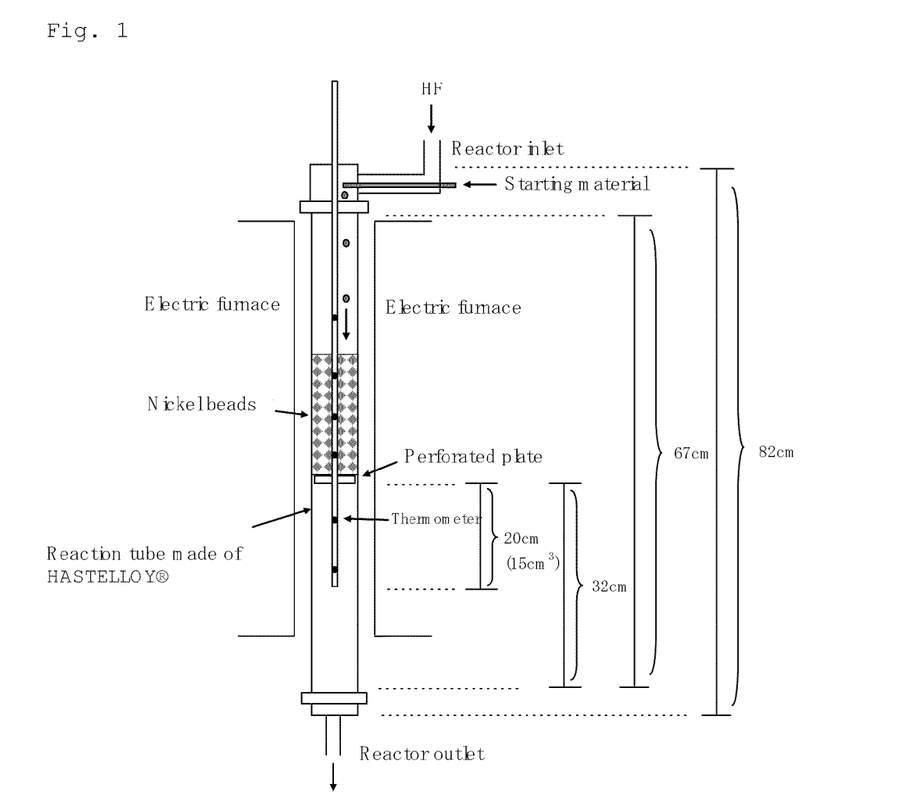
FIG. 1 shows the schematics of the reactor used in Examples 1 to 6.

A tubular reactor made of HASTELLOY®, having an inner diameter of 10 mm and a length of 82 cm was packed with 94.5 g of nickel beads (cylinder shaped, diameter: 2 mm; height: 2 mm) that were inactive in the reaction. The length of the packed nickel beads was 23 cm, and the void volume of this packed bed of the nickel beads was 6.9 $cm^3$. An insertion tube was introduced inside the reaction tube from the top to measure the temperature inside the reaction tube including the nickel bead-packed bed. FIG. 1 shows the schematics of the reactor. The reaction tube was maintained at atmospheric pressure (0.1 MPa) and a temperature of 400° C., and anhydrous hydrogen fluoride (HF) was continuously introduced into the reactor at 120 cc/min (flow rate at 0° C. and 0.1 MPa) for 0.5 hours. Thereafter, while continuing the supply of HF, 1,1,1,2,3-pentachloropropane (HCC-240db, purity: 99.6%) was continuously supplied at a rate of 6.0 cc/min (flow rate at 0° C. and 0.1 MPa) by adding 1,1,1,2,3-pentachloropropane dropwise in a liquid phase from the upper portion of the reaction tube, and the internal temperature of the nickel bead-packed bed was maintained at 400° C. to initiate the reaction. In this process, the temperature of the nickel bead-packed bed greatly exceeds the boiling point of 1,1,1,2,3-pentachloropropane (179° C./760 mmHg); thus, the 1,1,1,2,3-pentachloropropane is in a gas phase when passing through the nickel bead-packed bed.

During the reaction, nitrogen ($N_2$) was supplied at 80 cc/min (flow rate at 0° C. and 0.1 MPa) from the outlet side of the reactor, and was collected together with the reaction product. The internal temperature of the nickel bead-packed bed was measured at three points at equal intervals between the inlet side and the outlet side of the reaction tube; thereby, the average temperature was determined as a reaction temperature. The molar ratio of HF to 1,1,1,2,3-pentachloropropane (HF/1,1,1,2,3-pentachloropropane) was 20. The contact (residence) time ($V/F_0$) was calculated as 3.3 sec, based on the void volume (V) of the nickel bead-packed bed and the total flow rate ($F_0$) of the reactant. The internal temperature of the reaction tube at the point 5 cm above the upper surface of the nickel bead-packed bed was about 375° C., and the internal temperature at the point 15 cm below the bottom surface of the packed bed was about 365° C. Therefore, the void volume of about 15 $cm^3$, which is the volume corresponding to a length of 20 cm in which the nickel beads are not packed, was also considered to be included in the reaction field in addition to that of the nickel bead-packed bed. Based on this, the contact (residence) time ($V/F_0$) was recalculated. As a result, $V/F_0$ was 10.4 sec. The contact (residence) time ($V/F_0$) was calculated in the same manner as above in the other Examples.

The outflow from the reactor obtained 3 hours after the initiation of the reaction was analyzed by gas chromatography. Among the reaction products, high-boiling products having a boiling point of 50° C. or more were quantified in the manner described below. Specifically, HCFC-141b in which a predetermined amount of perchloroethylene had been dissolved as an internal standard substance was mixed with ice water to preliminarily subject it to liquid separation. The component obtained at the outlet of the reactor was bubbled in the HCFC-141b layer for a predetermined period of time so that an organic substance was extracted in the HCFC-141b layer, and the acid content of hydrogen fluoride and hydrogen chloride was dissolved in the ice water layer.

The extraction liquid was heated to 20° C., and the HCFC-141b layer was analyzed by gas chromatography (FID). As a column, a DB-1 (60 m) capillary column was used. Taking coefficient for gas chromatography into consideration, the amount of each product produced was converted into a molar ratio, based on the ratio of the detected area of each of the obtained products to the detected area of the perchloroethylene, which was the internal standard substance.

Comparatively, low-boiling products having a boiling point of 50° C. or less were quantified in the manner described below. Specifically, two washing columns that were connected in series and filled with water were jointed to the reactor outlet and immersed in a water bath to be preliminarily heated to 60° C. Thereafter, the reactor outflow was introduced into the washing columns to perform bubbling so as to wash the acid content. Then, the gas component, which had been dewatered through a $CaCl_2$ tube, was collected and analyzed by gas chromatography (FID). At this time, a predetermined amount of HFC-32 as an internal standard substance was introduced from the reactor outlet side, together with the reactor outflow, to the washing columns. As a column, a GS-GASPRO (60 m) capillary column was used. Taking coefficient for gas chromatography into consideration, the amount of each product produced was converted into a molar ratio, based on the ratio of the detected area of each of the obtained products to the detected area of the HFC-32, which was the internal standard substance. In the manner described above, the components from the reactor outlet were quantified. Table 1 shows the result.

The products obtained in this Example are shown below. Among the following seven compounds, the compounds other than HCFC-1233xf are precursors of HCFC-1233xf that can be recycled and reused as a starting material and are thus regarded as useful substances.

$CCl_2=CClCH_2Cl$ (HCC-1230xa)
$CCl_2CCl=CH_2$ (HCC-1230xf)
$CFCl_2CHClCH_2Cl$ (HCFC-241db)
$CFCl_2CCl=CH_2$ (HCFC-1231xf)
$CF_2ClCHClCH_2Cl$ (HCFC-242dc)
$CF_2ClCCl=CH_2$ (HCFC-1232xf)
$CF_2CCl=CH_2$ (HCFC-1233xf)

The following compounds are regarded as impurities produced in the reaction.

$CF_3CH=CH_2$ (HFC-1243zf)
$CF_3CH=CHCl$ (HCFC-1233zd)
$CF_3CCl=CHCl$ (HCFC-1223xd)

Example 2

The reaction was performed under the same conditions as in Example 1, except that the amount of the nickel beads packed was changed to 126 g. The length of the nickel bead-packed bed was 30.5 cm, and $V/F_0$ was calculated as 11.2 sec. Table 1 shows the results of the analysis with respect to the product obtained 3 hours after the initiation of the reaction (Example 2-1), and 27 hours after the initiation of the reaction (Example 2-2).

Example 3

The reaction was performed under the same conditions as in Example 1, except that the reaction temperature was changed to 375° C. Table 1 shows the results of the analysis with respect to the product obtained 3 hours after the initiation of the reaction.

Example 4

The reaction was performed under the same conditions as in Example 1, except that the flow rate of the anhydrous hydrogen fluoride (HF) supplied was changed to 60 cc/min (flow rate at 0° C. and 0.1 MPa). The molar ratio of HF to 1,1,1,2,3-pentachloropropane was 10, and $V/F_0$ was calculated as 19.4 sec. Table 1 shows the results of the analysis with respect to the product obtained 3 hours after the initiation of the reaction.

Example 5

The reaction was performed under the same conditions as in Example 1, except for using, as a filler packed into the reaction tube, 31.5 g of Hastelloy pellets (thickness: 1 mm; length: 3 mm; width: 3 mm) made of the same material as that of the reaction tube was used in place of the nickel beads. The length of the Hastelloy pellet-packed bed was 28 cm, and the void volume in this packed bed was 7.7 cm³; thus, $V/F_0$ was calculated as 10.8 sec. Table 1 shows the results of the analysis with respect to the product obtained 2 hours after the initiation of the reaction.

Example 6

The reaction was performed under the same conditions as in Example 2, except that the starting material used was changed to a mixture of 1,1,2,3-tetrachloropropene (HCC-1230xa) and 2,3,3,3-tetrachloropropene (HCC-1230xf) (HCC-1230xa:HCC-1230xf=38:62, purity: 99.9%). Table 1 shows the results of the analysis with respect to the product obtained 3 hours after the initiation of the reaction.

TABLE 1

| | Ex. 1 | Ex. 2-1 | Ex. 2-2 | Ex. 3 | Ex. 4 | Ex. 5 | Ex. 6 |
|---|---|---|---|---|---|---|---|
| Reaction Temperature (° C.) | 400 | 401 | 401 | 375 | 400 | 400 | 400 |
| Molar Ratio | 20 | 20 | 20 | 20 | 10 | 20 | 20 |
| $V/F_0$ (sec.) | 10.4 | 11.2 | 11.2 | 10.4 | 19.4 | 10.8 | 11.2 |
| Time passed after the initiation of the reaction (h) | 3 | 3 | 27 | 3 | 3 | 2 | 3 |
| Conversion Rate of the Starting Material (%) | 100 | 100 | 100 | 100 | 100 | 100 | 100 |
| Selectivity of Useful Material (%) | | | | | | | |
| HCC-1230xa | 0 | 0 | 0 | 2.8 | 0.6 | 0 | 0 |
| HCC-1230xf | 0 | 0 | 0 | 0.0 | 0 | 0 | 0 |
| HCFC-241db | 0 | 0 | 0 | 4.1 | 1.3 | 0.1 | 0 |
| HCFC-1231xf | 0 | 0 | 0 | 1.0 | 0.4 | 0 | 0 |
| HCFC-242dc | 6.7 | 2.4 | 2.6 | 28.7 | 19.7 | 9.3 | 3.7 |
| HCFC-1232xf | 0.1 | 0 | 0 | 0.7 | 2.0 | 0.8 | 0.2 |
| HCFC-1233xf | 91.8 | 96.3 | 95.9 | 61.6 | 73.4 | 88.6 | 94.8 |
| Selectivity of Impurities (%) | | | | | | | |
| HFC-1243zf | 0.3 | 0.3 | 0.3 | 0.2 | 0.5 | 0.3 | 0.3 |
| HCFC-1233zd | 0.5 | 0.4 | 0.5 | 0.4 | 0.9 | 0.4 | 0.4 |
| HCFC-1223xd | 0.1 | 0.1 | 0.1 | 0.1 | 0.2 | 0.1 | 0.1 |
| Others | 0.5 | 0.5 | 0.6 | 0.4 | 1.0 | 0.4 | 0.5 |

Example 7

Figure 2:
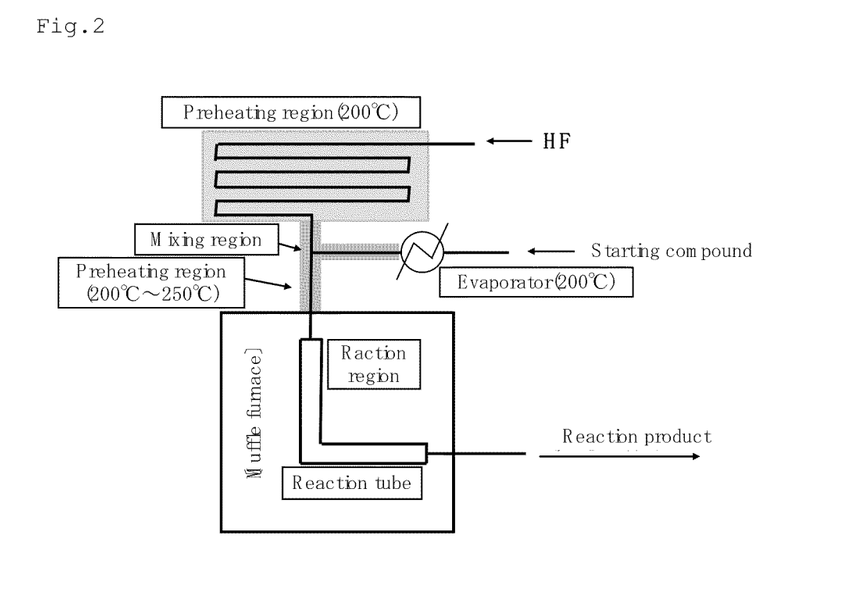
FIG. 2 shows the schematics of the reactor used in Examples 7 to 14.

FIG. 2 shows the schematics of a reactor used in Example 7. The reactor shown in FIG. 2 comprises a line for preheating and supplying anhydrous hydrogen fluoride (HF) in a gas phase; an evaporator and preheating line for a starting compound; a mixing region for mixing the starting compound with anhydrous hydrogen fluoride (HF) in a gas phase; a preheating line for heating the mixture of the starting compound and anhydrous hydrogen fluoride (HF) at the region between the mixing region and the inlet of a reaction tube; the reaction tube; and a muffle furnace. The reactor (reaction tube) was positioned entirely within the muffle furnace so as to keep the reaction temperature nearly uniform. The reaction tube was not packed with anything, and was used as a hollow reaction tube.

In the reactor used in Example 7, a tube made of INCONEL® 600, having an outer diameter of ⅛ inch (wall thickness: 0.7 mm) and a length of 10.4 m was used as the reaction tube; tubes made of HASTELLOY® 22 (outer: diameter ⅛ inch) were used at a joint region between the reaction tube and the mixing region, and as a reaction outlet line extending from the reaction tube; and a joint made of MONEL® was used for jointing. The volume of the reaction tube was 25.7 cm³. Within the muffle furnace, the volume of the joint region other than that of the reaction tube was small and was not considered as a reaction volume; therefore, the reaction volume (V), i.e., the volume of the reaction space, was determined as 25.7 cm³. The same applies to Examples 8 to 14.

The reaction tube was maintained at atmospheric pressure (0.1 MPa), and the muffle furnace at a temperature of 400° C. Nitrogen was continuously supplied to the reactor at 100 cc/min (flow rate at 0° C. and 0.1 MPa) for 15 hours. While continuing the supply of nitrogen, anhydrous hydrogen fluoride (HF) was continuously supplied to the reactor at 128 cc/min (flow rate at 0° C. and 0.1 MPa) for 1 hour. Then, while continuing the supply of HF, 1,1,1,2,3-pentachloropropane (HCC-240db, purity: 99.6%) was continuously supplied in a gas phase at 6.4 cc/min (flow rate at 0° C. and 0.1 MPa), and the amount of nitrogen supplied was changed to 6.4 cc/min (flow rate at 0° C. and 0.1 MPa); thereby, a reaction was initiated. The reaction pressure during the reaction was 0.02 MPa (gauge pressure). During the reaction, nitrogen ($N_2$) was supplied at 60 cc/min (flow rate at 0° C. and 0.1 MPa) from the outlet side of the reactor, and was collected together with the reaction product. The temperature of the outer wall of the reaction tube was measured at 5 points in total at equal intervals between the inlet side and the outlet side of the reactor, and the average temperature was regarded as a reaction temperature. The same measurement was performed in the Examples below to determine the reaction temperature.

The molar ratio of HF to 1,1,1,2,3-pentachloropropane (HF/1,1,1,2,3-pentachloropropane) was 20. The residence time ($V/F_0$) was calculated as 10.9 sec, based on the reaction volume (V) and the total flow rate ($F_0$) of the gas supplied to the reactor. In the Examples below, the residence time ($V/F_0$) was calculated in the same manner as above.

The outflow from the reactor outlet obtained 3 hours after the initiation of the reaction was analyzed by gas chromatography.

Among the reaction products, high-boiling products having a boiling point of about 50° C. or more were quantified in the same manner as in Example 1, except that the liquid for extracting the organic substance was changed from HCFC-141b to HCFC-225 (225ca:225cb=43:57), and the column used in the gas chromatography (FID) was changed from DB-1 (60 m) to DB-624 (60 m). Low-boiling products having a boiling point of 50° C. or less were quantified in the same manner as in Example 1. In the Examples 8 to 14, the quantification was performed using the same analytical process as described above.

Table 2 shows the reaction conditions and the results of the analysis.

Example 8

The same reactor used in Example 7 was prepared, except that the reaction tube was changed to a tube made of INCONEL® 600, having an outer diameter of ¼ inch (wall thickness: 1.0 mm) and a length of 164 cm. The volume of the reaction tube was 24.4 cm³, which was regarded as a reaction volume (V).

In this reactor, the reaction tube was maintained at atmospheric pressure (0.1 MPa), and the muffle furnace at a temperature of 400° C. Nitrogen was continuously supplied to the reactor at 100 cc/min (flow rate at 0° C. and 0.1 MPa) for 15 hours. The supply of nitrogen was subsequently stopped, and then anhydrous hydrogen fluoride (HF) at 200 cc/min (flow rate at 0° C. and 0.1 MPa) and 1,1,1,2,3-pentachloropropane (HCC-240db, purity: 99.6%) at 10.0 cc/min (flow rate at 0° C. and 0.1 MPa) were continuously supplied in a gas phase to the reactor for 10 hours. Thereafter, the supply of anhydrous hydrogen fluoride (HF) and 1,1,1,2,3-pentachloropropane was stopped, and nitrogen was supplied at 200 cc/min (flow rate at 0° C. and 0.1 MPa) again, to reduce the temperature in the muffle furnace. After the temperature in the reactor was reduced to room temperature, the supply of nitrogen was continued for another 10 hours.

Next, the reaction tube was maintained at atmospheric pressure (0.1 MPa) and the muffle furnace at a temperature of 400° C. Nitrogen was continuously supplied to the reactor at 100 cc/min (flow rate at 0° C. and 0.1 MPa) for 1 hour. While continuing the supply of nitrogen, anhydrous hydrogen fluoride (HF) was continuously supplied to the reactor at 140 cc/min (flow rate at 0° C. and 0.1 MPa) for 1 hour. Sequentially, while continuing the supply of HF, 1,1,1,2,3-pentachloropropane (HCC-240db, purity: 99.6%) was supplied at 7.0 cc/min (flow rate at 0° C. and 0.1 MPa) in a gas phase, and the amount of nitrogen supplied was changed to 7.0 cc/min (flow rate at 0° C. and 0.1 MPa); thereby, the reaction was initiated. The reaction was continued while the reaction conditions were maintained. The reaction pressure during the reaction was 0.01 MPa (gauge pressure). During the reaction, nitrogen ($N_2$) was supplied at 60 cc/min (flow rate at 0° C. and 0.1 MPa) from the reactor outlet side, and collected together with the reaction product. The molar ratio of HF to 1,1,1,2,3-pentachloropropane (HF/1,1,1,2,3-pentachloropropane) was 20, and the residence time ($V/F_0$) was 9.5 sec. Gas chromatography analysis was performed on the outflow from the reactor outlet obtained 15 hours after the initiation of the reaction (Example 8-1), 78 hours after the initiation of the reaction (Example 8-2), and 152 hours after the initiation of the reaction (Example 8-3). Table 2 shows each of the reaction conditions and the results of the analysis.

Example 9

The same reactor used in Example 7 was prepared using 5.2 m of the reaction tube that had been used for the duration of 12 hours in the experiment of Example 7. The volume of the reaction tube was 12.8 cm³, which was regarded as the reaction volume (V). In this reactor, the reaction tube was maintained at atmospheric pressure (0.1 MPa), and the muffle furnace at a temperature of 365° C. Nitrogen was continuously supplied to the reactor at 100 cc/min (flow rate at 0° C. and 0.1 MPa) for 3 hours. While continuing the supply of nitrogen, anhydrous hydrogen fluoride (HF) was continuously supplied to the reactor at 105 cc/min (flow rate at 0° C. and 0.1 MPa) for 1 hour. Sequentially, while continuing the supply of HF, 1,1,1,2,3-pentachloropropane (HCC-240db, purity: 99.6%) was supplied at 7.0 cc/min (flow rate at 0° C. and 0.1 MPa) in a gas phase, and the supply of nitrogen was stopped; thereby, the reaction was initiated. The reaction pressure during the reaction was 0.02 MPa (gauge pressure). During the reaction, nitrogen ($N_2$) was supplied at 60 cc/min (flow rate at 0° C. and 0.1 MPa) from the reactor outlet side, and was collected together with the reaction product. The molar ratio of HF to 1,1,1,2,3-pentachloropropane (HF/1,1,1,2,3-pentachloropropane) was 15, and the residence time ($V/F_0$) was 6.9 sec.

The outflow from the reactor outlet obtained 5 hours after the initiation of the reaction was analyzed by gas chromatography. Table 2 shows each of the reaction conditions and the results of the analysis.

Example 10

The same reactor used in Example 7 was prepared using, as a reaction tube, a tube made of INCONEL® 600 having an outer diameter of ½ inch (wall thickness of 1.24 mm), and a length of 120 cm. The volume of the reaction tube was 99.5 cm³, which was regarded as a reaction volume (V).

In this reactor, the reaction tube was maintained at atmospheric pressure (0.1 MPa), and the muffle furnace at a temperature of 400° C. Nitrogen was continuously supplied to the reactor at 200 cc/min (flow rate at 0° C. and 0.1 MPa) for 20 hours. The supply of nitrogen was subsequently stopped, and then anhydrous hydrogen fluoride (HF) at 200 cc/min (flow rate at 0° C. and 0.1 MPa) and 1,1,1,2,3-pentachloropropane (HCC-240db, purity: 99.6%) at 10.0 cc/min (flow rate at 0° C. and 0.1 MPa) were continuously supplied in a gas phase to the reactor for 20 hours. Thereafter, the supply of anhydrous hydrogen fluoride (HF) and 1,1,1,2,3-pentachloropropane was stopped, and nitrogen was supplied at 200 cc/min (flow rate at 0° C. and 0.1 MPa) again, to reduce the temperature in the muffle furnace. After the temperature was reduced to room temperature, the supply of nitrogen was continued for another 24 hours.

Next, the reaction tube was maintained at atmospheric pressure (0.1 MPa) and the muffle furnace at a temperature of 400° C. Nitrogen was continuously supplied to the reactor at 200 cc/min (flow rate at 0° C. and 0.1 MPa) for 3 hours. While continuing the supply of nitrogen, anhydrous hydrogen fluoride (HF) was continuously supplied to the reactor at 200 cc/min (flow rate at 0° C. and 0.1 MPa) for 1 hour. Sequentially, while continuing the supply of HF, 1,1,1,2,3-pentachloropropane (HCC-240db, purity: 99.6%) was supplied at 10.0 cc/min (flow rate at 0° C. and 0.1 MPa) in a gas phase, and the amount of nitrogen supplied was changed to 10.0 cc/min (flow rate at 0° C. and 0.1 MPa); thereby, the reaction was initiated. The reaction pressure during the reaction was 0.0 MPa (gauge pressure). During the reaction, nitrogen ($N_2$) was supplied at 80 cc/min (flow rate at 0° C. and 0.1 MPa) from the reactor outlet side, and was collected together with the reaction product. The molar ratio of HF to 1,1,1,2,3-pentachloropropane (HF/1,1,1,2,3-pentachloropropane) was 20, and the residence time ($V/F_0$) was 27.1 sec. The outflow from the reactor outlet obtained 7.5 hours after the initiation of the reaction was analyzed by gas chromatography. Table 2 shows each of the reaction conditions and the results of the analysis.

Example 11

The same reactor used in Example 7 was prepared, using, as a reaction tube, a tube made of HASTELLOY® 22, having an outer diameter of ¼ inch (wall thickness: 1.0 mm) and a length of 124 cm. The volume of the reaction tube was 18.4 cm³, which was regarded as a reaction volume (V).

In this reactor, the reaction tube was maintained at atmospheric pressure (0.1 MPa), and the muffle furnace at a temperature of 400° C. Nitrogen was continuously supplied to the reactor at 100 cc/min (flow rate at 0° C. and 0.1 MPa) for 15 hours. Then, the temperature in the muffle furnace was increased to 450° C., the supply of nitrogen was stopped, and anhydrous hydrogen fluoride (HF) at 200 cc/min (flow rate at 0° C. and 0.1 MPa) and 1,1,1,2,3-pentachloropropane (HCC-240db, purity: 99.6%) at 10.0 cc/min (flow rate at 0° C. and 0.1 MPa) were continuously supplied in a gas phase to the reactor for 10 hours. Thereafter, the supply of anhydrous hydrogen fluoride (HF) and 1,1,1,2,3-pentachloropropane was stopped, and nitrogen was supplied at 200 cc/min (flow rate at 0° C. and 0.1 MPa) again, to reduce the temperature in the muffle furnace. After the temperature was reduced to room temperature, the supply of nitrogen was continued for another 20 hours.

Next, the reaction tube was maintained at atmospheric pressure (0.1 MPa) and the muffle furnace at a temperature of 400° C. Nitrogen was continuously supplied to the reactor at 100 cc/min (flow rate at 0° C. and 0.1 MPa) for 1 hour. While continuing the supply of nitrogen, anhydrous hydrogen fluoride (HF) was continuously supplied to the reactor at 140 cc/min (flow rate at 0° C. and 0.1 MPa) for 1 hour. Sequentially, while continuing the supply of HF, 1,1,1,2,3-pentachloropropane (HCC-240db, purity: 99.6%) was supplied at 7.0 cc/min (flow rate at 0° C. and 0.1 MPa) in a gas phase, and the supply of nitrogen was stopped; thereby, the reaction was initiated. The reaction pressure during the reaction was 0.01 MPa (gauge pressure). During the reaction, nitrogen ($N_2$) was supplied at 60 cc/min (flow rate at 0° C. and 0.1 MPa) from the reactor outlet side, and was collected together with the reaction product. The molar ratio of HF to 1,1,1,2,3-pentachloropropane (HF/1,1,1,2,3-pentachloropropane) was 20, and the residence time ($V/F_0$) was 7.5 sec. The outflow from the reactor outlet obtained 3 hours after the initiation of the reaction was analyzed by gas chromatography. Table 2 shows each of the reaction conditions and the results of the analysis Example 12

Fluorination of Tetrachloropropene
(HCC-1230xa:HCC-1230xf=38:62)

The same reactor used in Example 11 was prepared, using a tube made of INCONEL® 600 having an outer diameter of ¼ inch (wall thickness of 1.0 mm) and a length of 124 cm as a reaction tube. The volume of the reaction tube was 18.4 cm³, which was regarded as a reaction volume (V).

In this reactor, the reaction tube was maintained at atmospheric pressure (0.1 MPa), and the muffle furnace at a temperature of 400° C. Nitrogen was continuously supplied to the reactor at 100 cc/min (flow rate at 0° C. and 0.1 MPa) for 15 hours. Then, the temperature in the muffle furnace was changed to 350° C., the supply of nitrogen was stopped, and anhydrous hydrogen fluoride (HF) at 200 cc/min (flow rate at 0° C. and 0.1 MPa) and a mixture of 1,1,2,3-tetrachloropropene (HCC-1230xa) and 2,3,3,3-tetrachloropropene (HCC-1230xf) (HCC-1230xa:HCC-1230xf=38:62, purity: 99.9%) at 10.0 cc/min (flow rate at 0° C. and 0.1 MPa) were continuously supplied in a gas phase to the reactor for 10 hours. Thereafter, the supply of anhydrous hydrogen fluoride (HF) and the mixture of 1,1,2,3-tetrachloropropene (HCC-1230xa) and 2,3,3,3-tetrachloropropene (HCC-1230xf) was stopped, and nitrogen was supplied at 200 cc/min (flow rate at 0° C. and 0.1 MPa) again, to reduce the temperature in the muffle furnace. After the temperature was reduced to room temperature, the supply of nitrogen was continued for another 10 hours.

Next, the reaction tube was maintained at atmospheric pressure (0.1 MPa) and the muffle furnace at a temperature of 320° C. Nitrogen was continuously supplied to the reactor at 100 cc/min (flow rate at 0° C. and 0.1 MPa) for 1 hour. While continuing the supply of nitrogen, anhydrous hydrogen fluoride (HF) was continuously supplied to the reactor at 105 cc/min (flow rate at 0° C. and 0.1 MPa) for 1 hour. Sequentially, while continuing the supply of HF, the mixture of 1,1,2,3-tetrachloropropene (HCC-1230xa) and 2,3,3,3-tetrachloropropene (HCC-1230xf) (HCC-1230xa:HCC-1230xf=38:62, purity: 99.9%) was supplied at 7.0 cc/min (flow rate at 0° C. and 0.1 MPa) in a gas phase, and the supply of nitrogen was stopped; thereby, the reaction was initiated. The reaction pressure during the reaction was 0.01 MPa (gauge pressure). During the reaction, nitrogen ($N_2$) was supplied at 60 cc/min (flow rate at 0° C. and 0.1 MPa) from the reactor outlet side, and was collected together with the reaction product. The molar ratio of HF to the tetrachloropropene mixture (HCC-1230xa:HCC-1230xf=38:62) (HF/(HCC-1230xa+HCC-1230xf)) was 15, and the residence time ($V/F_0$) was 9.9 sec. The outflow from the reactor outlet obtained 5 hours after the initiation of the reaction was analyzed by gas chromatography. Table 2 shows the reaction conditions and the results of the analysis.

Example 13

Fluorination of Tetrachloropropene
(HCC-1230xa:HCC-1230xf=38:62)

The reactor used in Example 12 was used as is, and the reaction was performed in the same manner as in Example 12, except that the reaction temperature was changed to 355° C.

Table 2 shows the results of the analysis with respect to the product obtained 5 hours after the initiation of the reaction.

Example 14

The same reactor used in Example 7 was prepared, using, as a reaction tube, a tube made of INCONEL® 600, having an outer diameter of ⅛ inch (wall thickness: 0.7 mm) and a length of 6.7 m. The volume of the reaction tube was 16.7 cm³, which was regarded as a reaction volume (V).

In this reactor, the reaction tube was maintained at atmospheric pressure (0.1 MPa), and the muffle furnace at a temperature of 400° C. Dry air ($N_2:O_2$=79:21) was continuously supplied to the reactor at 100 cc/min (flow rate at 0° C. and 0.1 MPa) for 10 hours. Subsequently, heating of the muffle furnace was stopped, and the flow rate of the dry air was changed to 30 cc/min (flow rate at 0° C. and 0.1 MPa). The dry air was allowed to pass through the reactor for 15 hours until the temperature decreased to room temperature. Thereafter, the supply of dry air was stopped, and nitrogen was supplied at 100 cc/min (flow rate at 0° C. and 0.1 MPa). The reaction tube was maintained at atmospheric pressure (0.1 MPa) and the muffle furnace at a temperature of 400° C. Anhydrous hydrogen fluoride (HF) at 140 cc/min (flow rate at 0° C. and 0.1 MPa) and 1,1,1,2,3-pentachloropropane (HCC-240db, purity: 99.6%) at 7.0 cc/min (flow rate at 0° C. and 0.1 MPa) were continuously supplied in a gas phase to the reactor, and the flow rate of nitrogen supplied was changed to 7.0 cc/min (flow rate at 0° C. and 0.1 MPa); thereby, the reaction was initiated. The reaction pressure during the reaction was 0.01 MPa (gauge pressure). During the reaction, nitrogen ($N_2$) was supplied at 60 cc/min (flow rate at 0° C. and 0.1 MPa) from the reactor outlet side, and was collected together with the reaction product. The molar ratio of HF to 1,1,1,2,3-pentachloropropane (HF/1,1,1,2,3-pentachloropropane) was 20, and the residence time (V/F$_0$) was 6.5 sec. The outflow from the reactor outlet obtained 3 hours after the initiation of the reaction was analyzed by gas chromatography. Table 2 shows each of the reaction conditions and the results of the analysis.

The invention claimed is:

1. A process for preparing 2-chloro-3,3,3-trifluoropropene comprising subjecting, in the absence of a catalyst, at least one chlorine-containing compound selected from the group consisting of chloropropane represented by formula (1): CClX$_2$CHClCH$_2$Cl, wherein each X is the same or different and each represents Cl or F, chloropropene represented by formula (2): CClY$_2$CCl=CH$_2$, wherein each Y is the same or different and each represents Cl or F, and chloropropene represented by formula (3): CZ$_2$=CClCH$_2$Cl, wherein each Z is the same or different and each represents Cl or F, to a reaction with hydrogen fluoride under heating in a gas phase.

2. The process for preparing 2-chloro-3,3,3-trifluoropropene according to claim 1, wherein the chlorine-containing compound used as a starting material is at least one compound selected from the group consisting of 1,1,1,2,3-pentachloropropane, 2,3,3,3-tetrachloropropene, and 1,1,2,3-tetrachloropropene.

3. The process for preparing 2-chloro-3,3,3-trifluoropropene according to claim 1, wherein the hydrogen fluoride is used in an amount of 5 to 30 mol relative to 1 mol of the chlorine-containing compound used as a starting material, and the reaction is carried out at 300° C. to 500° C.

4. A process for preparing 2-chloro-3,3,3-trifluoropropene, comprising the step of, after the preparation of 2-chloro-3,3,3-trifluoropropene in accordance with the process of claim 1, recycling at least one chlorine-containing compound contained in a product obtained during the preparation and selected from the group consisting of the chloropropane represented by formula (1): CClX$_2$CHClCH$_2$Cl, wherein each X is the same or different and each represents Cl or F, the chloropropene represented by formula (2): CClY$_2$CCl=CH$_2$, wherein each Y is the same or different and each represents Cl or F, and the chloropropene represented by formula (3): CZ$_2$=CClCH$_2$Cl, wherein each Z is the same or different and each represents Cl or F, as a starting compound.

5. The process for preparing 2-chloro-3,3,3-trifluoropropene according to claim 2, wherein the hydrogen fluoride is used in an amount of 5 to 30 mol relative to 1 mol of the

TABLE 2

|  | Ex. 7 | Ex. 8-1 | Ex. 8-2 | Ex. 8-3 | Ex. 9 | Ex. 10 | Ex. 11 | Ex. 12 | Ex. 13 | Ex. 14 |
| --- | --- | --- | --- | --- | --- | --- | --- | --- | --- | --- |
| Reaction Temperature (° C.) | 401 | 402 | 403 | 403 | 364 | 404 | 405 | 321 | 355 | 402 |
| Molar Ratio | 20 | 20 | 20 | 20 | 15 | 20 | 20 | 15 | 15 | 20 |
| V/F$_0$ (sec) | 10.9 | 9.5 | 9.5 | 9.5 | 6.9 | 27.1 | 7.5 | 9.9 | 9.9 | 6.5 |
| Time passed after the initiation of the reaction (h) | 3 | 15 | 78 | 152 | 5 | 7.5 | 3 | 5 | 5 | 3 |
| Conversion Ratio of the Starting Material (%) | 100 | 99.9 | 100 | 100 | 100 | 100 | 100 | 100 | 100 | 100 |
| Selectivity of Useable Material (%) | | | | | | | | | | |
| HCC-1230xa | 0 | 0.9 | 0 | 0.1 | 0 | 0.7 | 0.1 | 0 | 0 | 0 |
| HCC-1230xf | 0 | 0 | 0 | 0 | 0 | 0 | 0 | 0 | 0 | 0 |
| HCFC-241db | 0 | 3.2 | 0.1 | 0.1 | 0.3 | 1.1 | 0.3 | 0 | 0 | 0 |
| HCFC-1231xf | 0 | 0.9 | 0 | 0.0 | 0.1 | 0.4 | 0.4 | 1.1 | 0.4 | 0 |
| HCFC-242dc | 3.2 | 3.3 | 3.9 | 4.1 | 4.4 | 10.4 | 1.5 | 1.1 | 0.7 | 2.9 |
| HCFC-1232xf | 0.2 | 5.9 | 0.2 | 0.4 | 3.2 | 5.7 | 3.9 | 3.7 | 1.2 | 0.1 |
| HCFC-1233xf | 95.7 | 83.9 | 94.8 | 94.4 | 91.4 | 79.9 | 92.6 | 92.1 | 94.1 | 95.4 |
| Selectivity of Impurities (%) | | | | | | | | | | |
| HFC-1243zf | 0.4 | 0.7 | 0.4 | 0.4 | 0.3 | 0.6 | 0.4 | 0.1 | 0.1 | 0.1 |
| HCFC-1233zd | 0.2 | 0.4 | 0.2 | 0.2 | 0.1 | 0.3 | 0.2 | 0 | 0 | 0.1 |
| HCFC-1223xd | 0 | 0.2 | 0.1 | 0.1 | 0 | 0.2 | 0.1 | 0.3 | 0.4 | 0 |
| Others | 0.3 | 0.6 | 0.3 | 0.2 | 0.2 | 0.7 | 0.5 | 1.6 | 3.1 | 1.4 | chlorine-containing compound used as a starting material, and the reaction is carried out at 300° C. to 500° C.

6. A process for preparing 2-chloro-3,3,3-trifluoropropene, comprising the step of, after the preparation of 2-chloro-3,3,3-trifluoropropene in accordance with the process of claim 2, recycling at least one chlorine-containing compound contained in a product obtained during the preparation and selected from the group consisting of the chloropropane represented by formula (1): $CClX_2CHClCH_2Cl$, wherein each X is the same or different and each represents Cl or F, the chloropropene represented by formula (2): $CClY_2CCl$=$CH_2$, wherein each Y is the same or different and each represents Cl or F, and the chloropropene represented by formula (3): $CZ_2$=$CClCH_2Cl$, wherein each Z is the same or different and each represents Cl or F, as a starting compound.

7. A process for preparing 2-chloro-3,3,3-trifluoropropene, comprising the step of, after the preparation of 2-chloro-3,3,3-trifluoropropene in accordance with the process of claim 3, recycling at least one chlorine-containing compound contained in a product obtained during the preparation and selected from the group consisting of the chloropropane represented by formula (1): $CClX_2CHClCH_2Cl$, wherein each X is the same or different and each represents Cl or F, the chloropropene represented by formula (2): $CClY_2CCl$=$CH_2$, wherein each Y is the same or different and each represents Cl or F, and the chloropropene represented by formula (3): $CZ_2$=$CClCH_2Cl$, wherein each Z is the same or different and each represents Cl or F, as a starting compound.

8. A process for preparing 2-chloro-3,3,3-trifluoropropene, comprising the step of, after the preparation of 2-chloro-3,3,3-trifluoropropene in accordance with the process of claim 5, recycling at least one chlorine-containing compound contained in a product obtained during the preparation and selected from the group consisting of the chloropropane represented by formula (1): $CClX_2CHClCH_2Cl$, wherein each X is the same or different and each represents Cl or F, the chloropropene represented by formula (2): $CClY_2CCl$=$CH_2$, wherein each Y is the same or different and each represents Cl or F, and the chloropropene represented by formula (3): $CZ_2$=$CClCH_2Cl$, wherein each Z is the same or different and each represents Cl or F, as a starting compound.

* * * * *